United States Patent
Stonehouse et al.

(10) Patent No.: US 7,462,168 B2
(45) Date of Patent: Dec. 9, 2008

(54) SAFETY PEN NEEDLE WITH PASSIVE SAFETY SHIELD SYSTEM

(75) Inventors: David R. Stonehouse, Cambridge (GB); Eric D. Listenberger, Morristown, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 11/626,205

(22) Filed: Jan. 23, 2007

(65) Prior Publication Data

US 2008/0177237 A1    Jul. 24, 2008

(51) Int. Cl.
*A61M 5/32* (2006.01)
(52) U.S. Cl. ...................... 604/198; 604/192
(58) Field of Classification Search .......... 604/110, 604/198, 192, 187, 263, 111, 193, 194, 195, 604/196, 197, 207, 208, 209, 210, 211, 242, 604/506
See application file for complete search history.

(56) References Cited

U.S. PATENT DOCUMENTS

| | | | |
|---|---|---|---|
| 5,030,209 A * | 7/1991 | Wanderer et al. ........... 604/198 |
| 5,403,286 A | 4/1995 | Lockwood, Jr. ............. 604/110 |
| 5,423,758 A | 6/1995 | Shaw ........................ 604/110 |
| 5,545,145 A | 8/1996 | Clinton et al. .............. 604/192 |
| 5,658,259 A * | 8/1997 | Pearson et al. ............. 604/232 |
| 5,725,508 A | 3/1998 | Chanoch et al. ............. 604/507 |
| 5,827,232 A | 10/1998 | Chanoch et al. ............. 604/208 |
| 5,893,845 A * | 4/1999 | Newby et al. ............... 604/198 |
| 5,928,205 A | 7/1999 | Marshall ..................... 604/263 |
| 5,941,857 A | 8/1999 | Nguyen et al. .............. 604/263 |
| 5,964,739 A * | 10/1999 | Champ ........................ 604/263 |
| 6,379,337 B1 | 4/2002 | Mohammad ................. 604/195 |
| 6,547,764 B2 * | 4/2003 | Larsen et al. ............... 604/192 |
| 6,595,931 B2 * | 7/2003 | Ranford ...................... 600/573 |
| 6,986,760 B2 * | 1/2006 | Giambattista et al. ....... 604/198 |
| 7,104,969 B2 | 9/2006 | Du Plessis .................. 604/110 |

(Continued)

FOREIGN PATENT DOCUMENTS

EP    724890 A1 *  8/1996

(Continued)

*Primary Examiner*—Kevin C Sirmons
*Assistant Examiner*—Shefali D Patel
(74) *Attorney, Agent, or Firm*—Alan W. Fiedler; Fitzpatrick, Cella, Harper & Scinto LLP

(57) ABSTRACT

A pen needle shield system according to the invention comprises at least an injection end shield positioned on the injection side of the hub, shielding the injection end of the needle after an injection, or in the event of an accidental triggering. The injection end shield is compressed toward the hub against the pressure of a biasing spring. The injection end shield engages a sleeve, which is arranged coaxially on the hub such that after the injection is administered the biasing spring pushes the injection end shield to cover the injection end of the needle, carrying the sleeve with it. The sleeve engages the hub, locking out the injection end shield in a position in which the injection end of the needle is covered by the injection end shield. The system also may incorporate a non-injection end shield that engages with the hub when a pen injector is unscrewed from the hub to lock out the non-injection end shield in the position protecting the non-injection end of the needle.

7 Claims, 6 Drawing Sheets

U.S. PATENT DOCUMENTS

| | | | |
|---|---|---|---|
| 2003/0060776 A1 | 3/2003 | Heiniger | 604/198 |
| 2005/0038392 A1 | 2/2005 | DeSalvo | 604/198 |
| 2005/0171485 A1 | 8/2005 | Larsen et al. | 604/198 |
| 2006/0189933 A1* | 8/2006 | Alheidt et al. | 604/110 |

FOREIGN PATENT DOCUMENTS

| | | |
|---|---|---|
| WO | 2006111862 | 10/2006 |

* cited by examiner

SAFETY PEN NEEDLE WITH PASSIVE SAFETY SHIELD SYSTEM

BACKGROUND OF THE INVENTION

1. Field of the Invention

The invention is directed to a passive safety shield system which may be associated with a pen needle to protect the patient and/or healthcare professional using the pen needle from accidental needlesticks from the injection end and the non-injection end of the needle.

2. Description of the Related Art

Accidental needlestick injuries from contaminated needles expose healthcare workers to the risk of infection from blood-borne pathogens, including the viruses that cause hepatitis B and C, and HIV. According to the Centers for Disease Control and Prevention, healthcare workers in the United States experience an estimated 600,000 exposures to blood each year, with RNs being subject to an overwhelming majority of these incidents.

While the injection device of choice in the U.S. remains the syringe, the demand for pen needles is growing rapidly. The use of self-injection pen needle devices is increasing due to the relative convenience, portability, and ease of use of these devices as compared to single use syringes. Pen needles are also becoming more commonplace in the hospital/clinical setting, as certain drugs, such as human growth hormone and osteoporosis medications, are available only in pen needle format.

Healthcare workers have sustained needlestick injuries while removing and disposing of pen needles from injection devices after administering an injection to patients. The needles are typically removed after each injection to minimize contamination of the medication in the cartridge and to prevent needle re-use. Removal of the needle generally requires the re-shielding of the needle using the outer protective shield in which it was supplied and it is especially during the re-shielding step where injuries can occur. Needlestick injuries also occur during the removal of pen needles that have not been re-shielded.

U.S. Pat. No. 6,986,760 B2, assigned to the assignee of the present application, the disclosure of which is herein incorporated by reference in its entirety, teaches a pen needle and safety shield system wherein a safety shield, which normally encloses the needle cannula prior to use, permits retraction of the safety shield during injection and automatically extends and locks the shield in the extended enclosed position following use. The pen needle also prevents retraction of the shield during assembly of the shield and needle cannula and hub assembly on the pen injector.

The present invention includes a shield system for the injection end of the needle. A sleeve cooperates with the hub and with the injection end shield to hold the sleeve in a position covering the needle before an injection, and to lock the shield in a position covering the needle after an injection or in the event of an accidental triggering. In embodiments, a non-injection end shield is provided which prevents needle stick injuries at the non-injection end of the needle, which might otherwise occur before a pen injector is inserted, or after removal.

SUMMARY OF THE INVENTION

An injection pen needle according to the invention includes an automatic or "passive" safety shield system. In a first aspect, the invention is a novel shield system for the injection end of the needle. The needle is mounted on a hub. An injection end shield, having an aperture to permit passage of the needle through the shield, situated on and moving coaxially on the hub, is biased with a spring toward the injection end of the needle. In use, the shield slides toward the non-injection end of the hub and engages a sleeve having fastening elements cooperating with corresponding elements on the shield to fasten the shield to the sleeve.

The sleeve also has hub fastening elements engaging corresponding elements on the hub. Thus, the sleeve engages to the hub in two positions. The sleeve may be temporarily retained on a first retaining element on the hub in a first position, before the injection is administered. This prevents an accidental needlestick until an ample injection force is applied to the endwall of the shield against the patient's body. After the injection is administered, or in the event of an accidental triggering, the hub, sleeve and shield interact to permanently lock out the shield in a protecting position.

In another aspect of the invention, the system includes automatic or "passive" shields for both the injection end and the non-injection end of the needle. The injection-end shield is as described above. The non-injection end shield is situated on the hub in a recess surrounding the non-injection end of the needle and is provided with an aperture allowing the non-injection end of the needle to access medicament in the pen injector. The non-injection end shield is provided with at least one engaging element to engage a corresponding element on the hub, such that, when the pen injector is removed from the hub, the non-injection end shield locks out against the hub in a position covering the non-injection end of the needle.

DETAILED DESCRIPTION OF THE PREFERRED EMBODIMENTS

The safety shield system according to the invention is "passive" because shielding of the injection end of the needle is automatic upon administering an injection, or upon triggering the pen needle in the case of an accidental use. Likewise, shielding of the non-injection end is automatic upon removing the pen-injector. User-implemented steps are not required to shield the needle. The two shields on either side of the needle operate independently, but together constitute a shield "system." The shield on the injection end cooperates with the sleeve and hub and therefore by itself also constitutes a "system." The terms "injection end" and "non-injection end" refer to directions on the device. The injection end refers to a direction toward the end of the device that is normally pressed against a patient's body during an injection (the distal end), while the non-injection end refers to the opposite direction, toward the proximal end.

A pen needle generally has a longest dimension and a small width relative to its length. Movement on the longitudinal axis is referred to herein as "axial" movement. The perpendicular direction is referred to as the "radial" direction. A pen needle according to the invention typically is generally cylindrical, but need not be. A "tubular" element in this context means simply an element with openings at opposite sides.

As used herein, the injection end shield and the non injection end shield "cover" the respective ends of the needle when the tip of the needle does not extend beyond the end wall of the respective shield, notwithstanding that the tip of the needle may be quite close to the aperture in the respective shields, and exposed to view.

Figure 1:
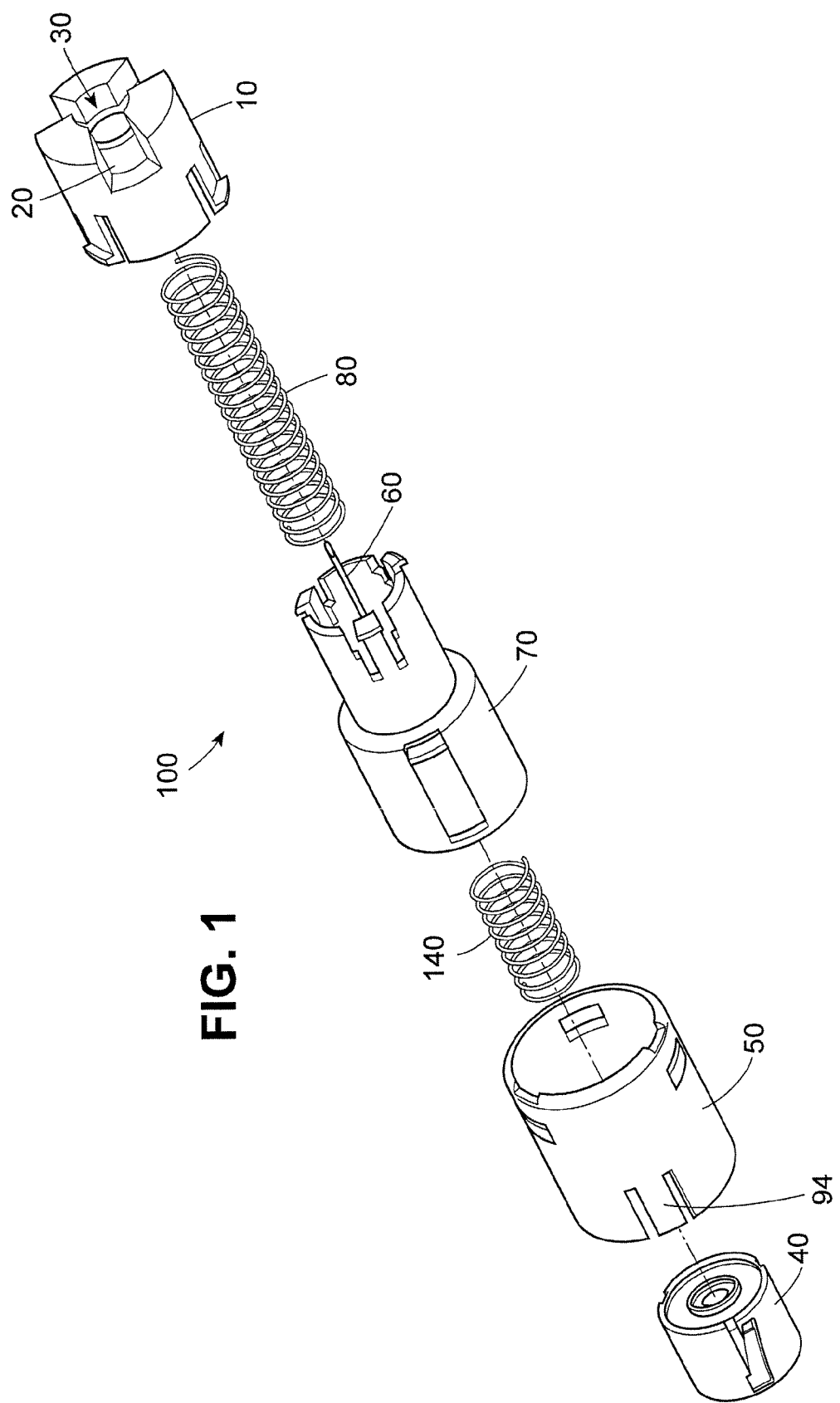
FIG. 1 is an exploded view of the safety shield system according to an embodiment of the invention.

In the exploded view of FIG. 1, an embodiment of a passive safety shield system 100 is shown, wherein injection end shield 10 provides protection from accidental needlesticks by covering the injection end of needle 60 once the passive safety features have been triggered. After injection, or after an accidental triggering, the shield 10 is locked out against the hub 70 by the interlocked sleeve 50, as described below.

Shield 10, which is typically an injection molded plastic part, comprises a central aperture 30 for passage of the needle. To aid priming, the shield may have a number of cut-outs 20, which allow a view of the needle's tip. In the embodiment shown in FIG. 1, three slots 20 are shown positioned around the top of the shield. In other embodiments, cut-outs may be positioned opposite each other on the shield, allowing an unrestricted view past the needle.

Figure 2:
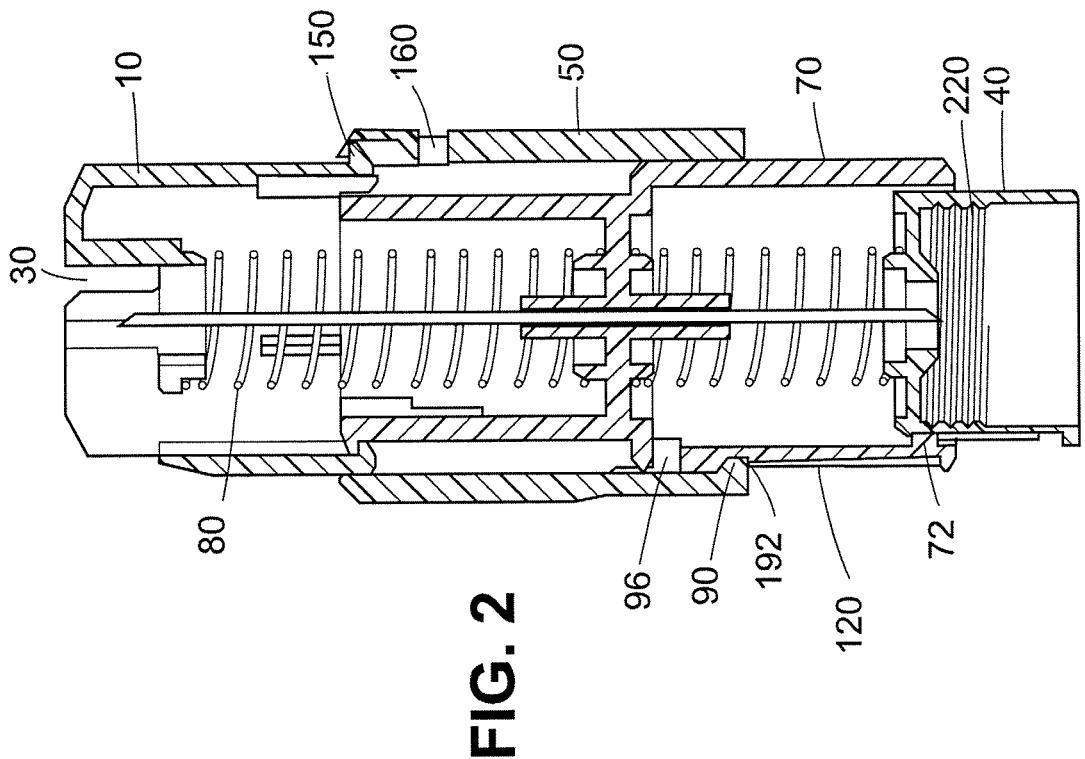
FIG. 2 is a detail of the safety shield system according to an embodiment of the invention in a ready-to-use position.

The hub 70 is typically an injection-molded plastic housing that supports needle 60. As seen in FIG. 2, a compression spring 80 is positioned between the base of the hub 70 and against ribs in the shield 10, thereby biasing the shield toward the injection end of the needle. Thus, as the shield 10 moves toward the hub 70 during the injection, the spring 80 becomes compressed.

In the embodiment shown in FIG. 2, shield 10 slides inside the sleeve 50, both elements being arranged coaxially on the hub. Sleeve 50 moves along the hub such that when the shield 10 is fully depressed it becomes locked to the sleeve, with shield fastening elements. In the embodiment shown, shield fastening elements include one or more radial snaps 150 on the base of the shield which engage one or more corresponding cut-outs 160 in the sleeve, such that if the shield is depressed further, the sleeve is forced to move axially on the hub in tandem with the shield. According to one embodiment, the shield moves toward the non-injection end a distance of about 3 mm before the radial snaps 150 engage cut-outs 160. At this stage the needle does not emerge from the central aperture 30.

Figure 3:
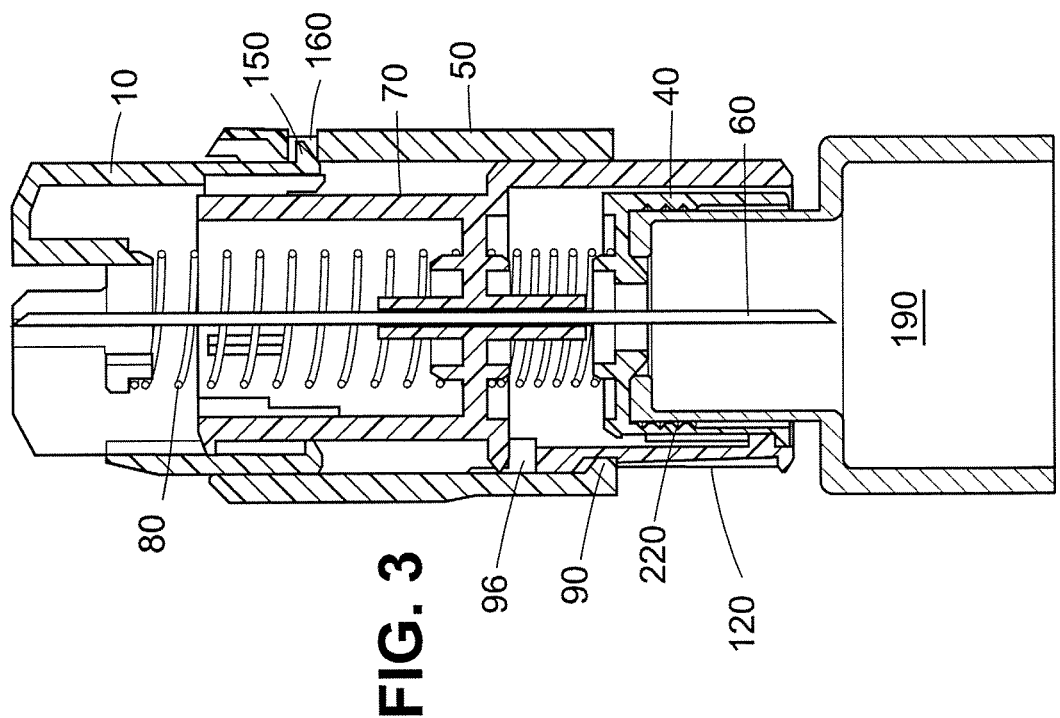
FIG. 3 is a detail of the safety shield system according to an embodiment the invention, in a position attained during an initial stage of an injection or accidental use.

In FIG. 3, the passive shield system is shown in the state obtained just prior to an injection being administered or after an accidental triggering. At this point, the needle tip is just about to emerge from the shield 10, and the shield 10 is locked to the sleeve as a result of interlocked snap 150 and cut-out 160. If at this point the pressure is removed from the shield, the sleeve, which is locked to the shield, moves along the hub in the direction of the injection end, biased by spring 80. The shield locks out when tab 90 engages lock out recess 96 in the hub. This engagement prevents the shield from moving relative to the hub to re-expose the patient end needle tip after an accidental triggering. If the injection is continued, as a result of alignment tab 90 being temporarily retained in position by retaining recess 192 in the hub, the shield and sleeve are temporarily prevented from moving, as a greater force, such as may be applied by pressing the end wall of the shield against a patient's skin to administer an injection, is required to overcome the retaining force and to allow tab 90 to proceed down track 120.

Sleeve 50 is likewise preferably an injection molded plastic part, assembled coaxially on the outside of hub 70 with at least one hub fastening element cooperating with a corresponding element on the hub. As an example of a hub fastening element, alignment tab 90 on the end of the sleeve is preferably on a flexible arm 94 of the sleeve, allowing the tab to temporarily engage retaining recess 192 to restrain axial movement of the sleeve when the shield is depressed during the start of an injection or an accidental use, and on the return stroke, to more permanently engage hub lock out recess 96 to prevent axial movement of the shield altogether, while it is locked to the hub.

Additional elements, including further protrusions and recesses, may be added to further limit relative motion of the hub, sleeve and shield, without in any way limiting the foregoing description.

Figure 4:
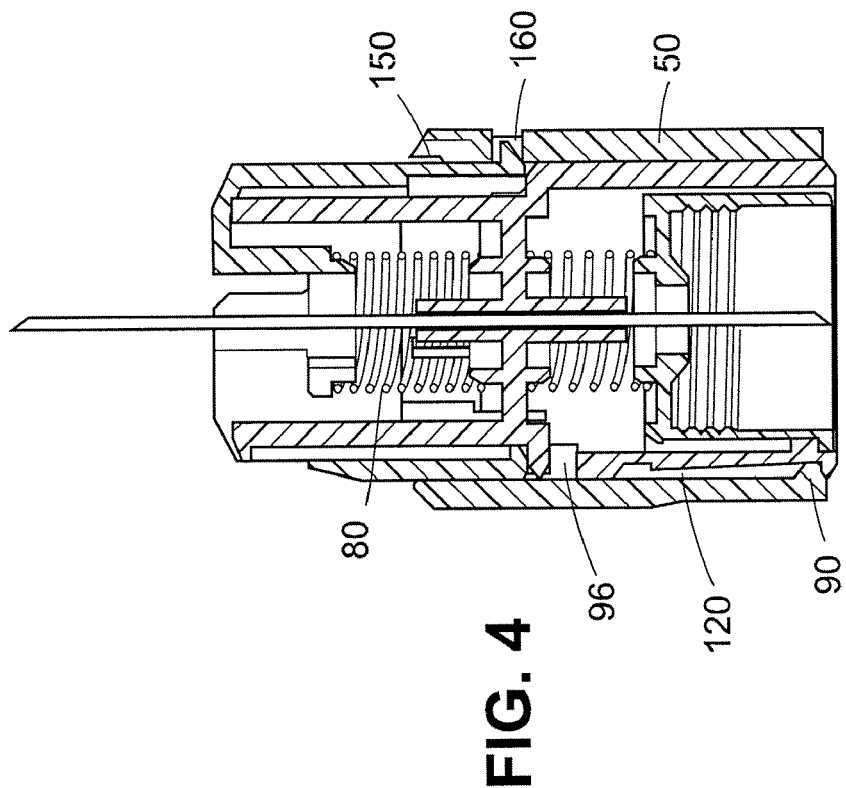
FIG. 4 is a detail of the safety shield system according to an embodiment of the invention, in a position with the injection end shield fully compressed against the biasing spring, and engaging the sleeve, such as would be attained during an injection.

In FIG. 4, shield 10 is shown fully compressed, as it would be when exposing the effective length of the needle to the patient during an injection. At this point the spring 80 is fully compressed, radial snaps 150 are interlocked with cut outs 160 in the sleeve 50 and the alignment tab 90 on the sleeve are at the full travel position within the track 120 in the hub 70.

Figure 5:
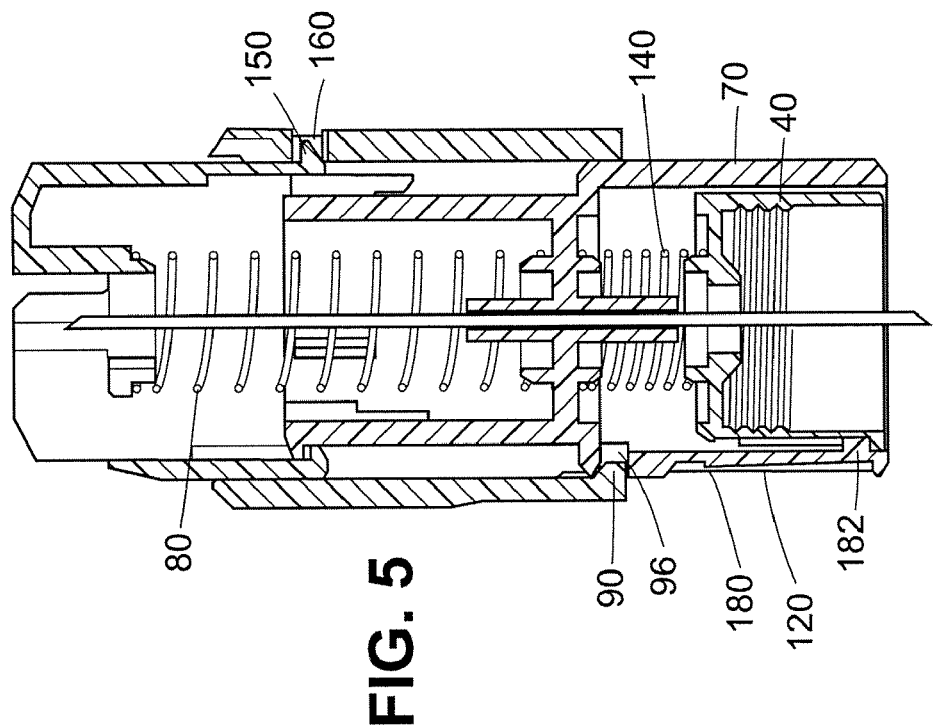
FIG. 5 is a detail of the safety shield system according to an embodiment of the invention after an injection, showing the injection end shield fully biased away from the hub, in a position covering the injection end of the needle.

As shown in FIG. 5, after an injection has been administered, and when the pressure is removed from the shield, the sleeve, which is locked to the shield, moves along the hub in the direction of the injection end, biased by spring 80. The shield locks out when tab 90 engages lock out recess 96 in the hub. This engagement prevents the shield from moving relative to the hub to re-expose the patient end needle tip after an injection has been administered. The device is then ready for disposal.

The non-injection end shield may be described in conjunction with the same Figures. In FIG. 1, the non-injection end shield 40 provides protection from accidental needlesticks at the non-injection end of the needle both prior to insertion of the pen injector and after the passive safety features have been triggered by removing the pen injector, as described below.

In FIG. 2, non-injection end shield 40 sits pointing outward of the recess on the non-injection end of the hub 70, providing a protective protruding rim and preventing finger access to the needle. As shown in FIG. 3, the pen injector 190 may be screwed into the non-injection end shield 40, and the shield can then be moved forward to engage the needle 60 with the pen injector's septum. In preferred embodiments, the pen injector is engaged via a threaded connection 220 on the non-injection end shield 40. The non-injection end shield is retained in the base of the hub 70, such that the pen injector can be attached by first screwing it into the non-injection end shield, and then pressing it forward to pierce the pen injector's septum, or by pushing it forward into the hub 70 to engage the pen's septum and then screwing it on to the non-injection end shield to mechanically connect it to the pen injector.

Figure 7:
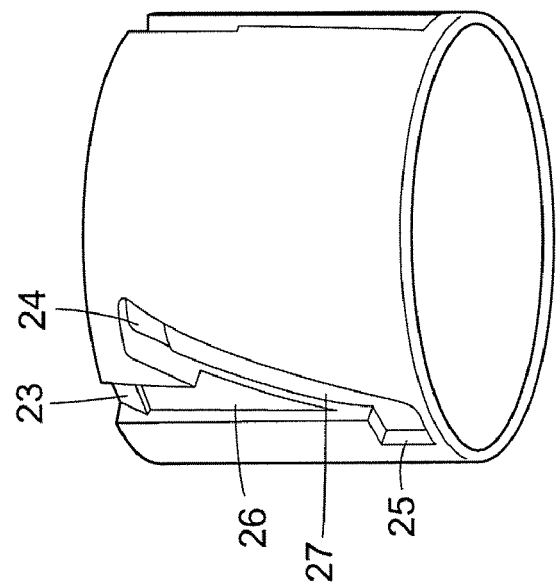
FIG. 7 is a perspective view of the non-injection end shield showing cam tracks and lockout mechanism.
Figure 6:
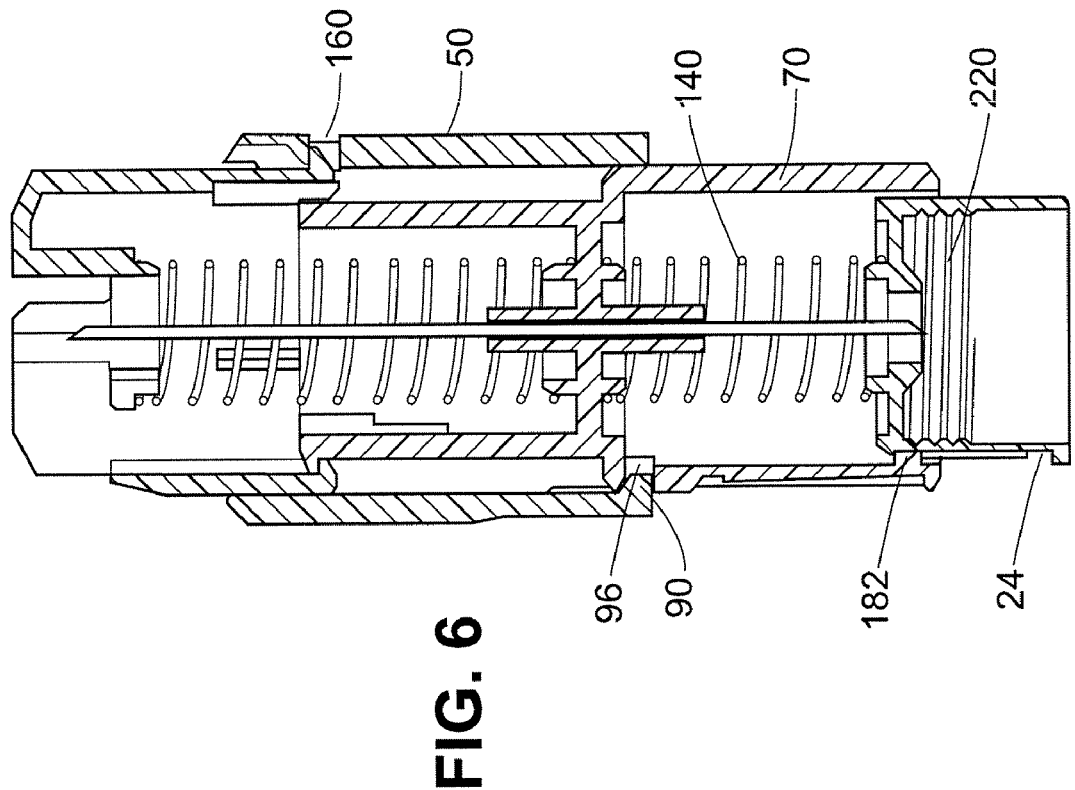
FIG. 6 is a detail of the safety shield system according to an embodiment of the invention after the pen injector is removed, with the injection end shield fully biased away from the hub, in a position covering the injection end of the needle, and the non-injection end shield covering the non-injection end of the needle, in the locked position.

An embodiment of the non-injection end shield is shown in FIG. 7, wherein cam tracks 26 and 27 constitute the engaging elements on non-injection end shield cooperating with at least one protrusion 182 on the hub to dictate the movement and lockout of the shield. A first cam track 26 runs in a substantially axial direction, and together with cut-out 23, enables the shield 40 to be pushed over the protrusion 182 and axially into the hub. The shield is thereafter retained in position by a portion 26 of the cam track cooperating with protrusion 182. As the pen injector is inserted into the non-injection end shield and then turned to engage the threads or is turned and pushed forward following the engagement of the threads, protrusion 182 on the hub enters detail 25 at the end of cam track 26 and retains the non-injection end shield in the inward position. On removal of the pen injector with an unscrewing motion, protrusion 182 engages curved cam track 27. At the end of the curved path, the protrusion meets depression 24, causing the shield to lock out in a position covering the non-injection end of the needle. After the shield 40 reaches the end of its cam track, the pen injector can be removed from the shield by continuing to unscrew it.

Optionally, second spring 140 assists the return of the shield 40 after an injection has been administered to ensure that it becomes fully deployed and locked out as the pen injector is removed, and also ensuring that the non-injection end shield covers the non-injection of the needle before the pen injector is installed.

Figure 8A:
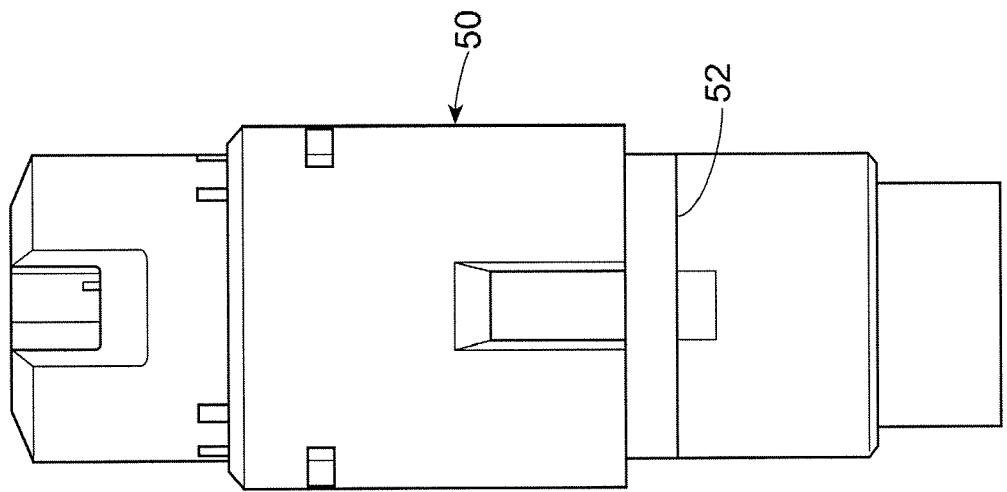
FIG. 8A and FIG. 8B show the position of the sleeve before and after activation.
Figure 8B:
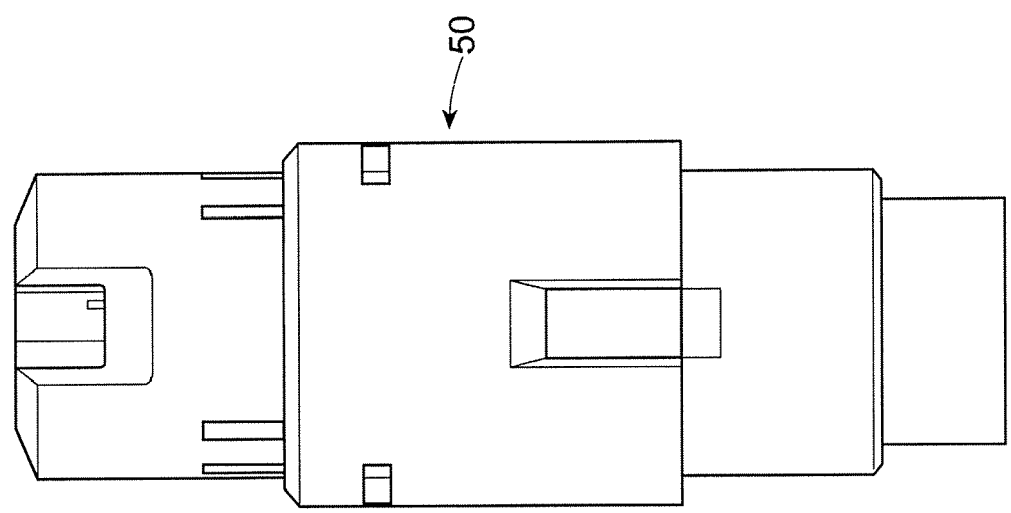

FIG. 8A shows the device before use, and FIG. 8B shows the device with the pen injector removed, in the full lockout position. Although the overall height of the device has remained unchanged, the relative position of the sleeve 50 has moved up with respect to the hub. This change of state can be used to indicate that the device has been used or augmented, such as by exposing a graphic or other indicator 52 which is revealed when the sleeve 50 slides up as shown in FIG. 8B.

Figure 9A:
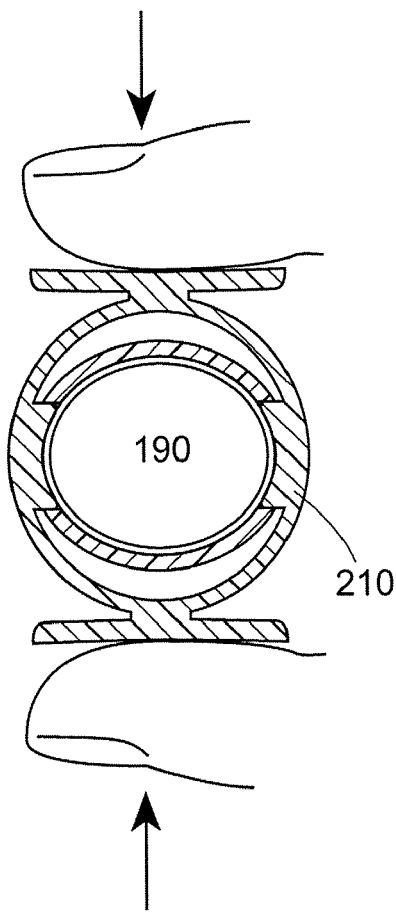
FIG. 9A and FIG. 9B show cross sectional details of a hub design according to an embodiment of the invention permitting connection of the hub to the pen injector.
Figure 9B:
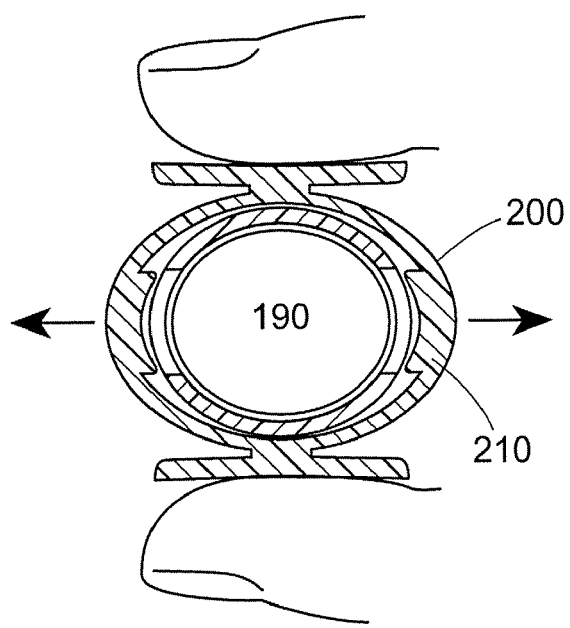
Figure 9C:
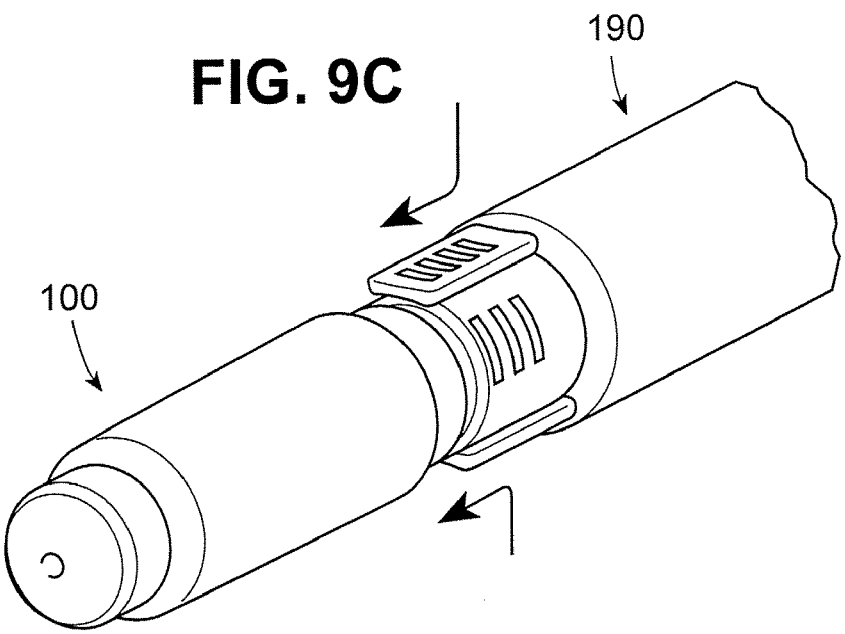
FIG. 9C shows a perspective view of the embodiment of FIG. 9A and FIG. 9B including a connection of the hub to the pen injector.

FIG. 9A, FIG. 9B and FIG. 9C show an alternative pen needle wherein removal may be effected using one hand. The pen needle housing 200 can be held onto the pen injector 190 by means of a number of interlocking elements on the injector pen 220 and the pen needle 210. These may be disengaged by squeezing the housing 200 as shown, such that the pen injector is freed from gripping elements 210. The pen injector may then be slid off in the direction of the arrows. Elements other than threads may then be used to engage the non-injection end shield 40 with the hub 70 in the locked out position. In another embodiment the non-injection end shield 40 with the hub 70 may be combined, offering no non-injection protection but allowing for the pen needle to be removed from the pen injector one-handed.

The foregoing description of the preferred embodiments is for the purposes of illustration, and is not to be considered as limiting the invention, which is defined by the appended claims. It will be understood by those of ordinary skill in the art, for example, in connection with the present disclosure that the relative positions of a positive feature (tab, protrusion, or the like) on a first element, engaging a corresponding negative feature (recess, cutout, through-hole, or the like) on a second element, may be reversed, so that the negative feature appears on the first element and the positive feature appears on the second element. Likewise, those of ordinary skill in the art will understand that typical features, including for example, recesses, cutouts, and through-holes, may be interchangeable.

What is claimed is:

1. A passive safety shield system for an injection pen needle, comprising:
   a needle hub;
   a needle mounted on the hub and having an injection end and a non-injection end, wherein the hub has a recess surrounding the non-injection end of the needle to receive a pen-injector;
   an injection end shield moving coaxially on the hub and having an aperture to permit passage of the needle through the injection end shield;
   a substantially tubular sleeve moving coaxially on the hub;
   a shield fastening element on the sleeve cooperating with a corresponding element on the injection end shield to fasten the injection end shield to the sleeve;
   a hub fastening element on the sleeve cooperating with a corresponding element on the hub to fasten the hub to the sleeve;
   a spring biasing the injection end shield toward the injection end of the pen needle;
   wherein the sleeve is engaged with the hub and the injection end shield to hold the injection end shield in a position covering the injection end of the needle before an injection, and to lock the injection end shield in a position covering the injection end after an injection or in the event of an accidental use; and
   wherein the hub fastening element on the sleeve comprises a flexible arm having an alignment tab which cooperates with a first retaining recess at a first axial position on the hub and a second lockout recess at a second axial position on the hub.

2. The system of claim 1, wherein said shield fastening element on the sleeve comprises at least one cutout on the sleeve cooperating with a corresponding snap on the injection end shield to fasten the injection end shield to the sleeve in a locked out position, with the injection end shield covering the injection end of the needle.

3. The system of claim 1, wherein the hub, injection end shield, and sleeve are injection molded plastic parts.

4. The system of claim 1, wherein sliding movement of the sleeve is an indicator or exposes an indicator to indicate triggering of the pen needle safety shield system.

5. The system of claim 1, wherein the injection end shield is provided with cut outs on the end thereof exposing the needle to view.

6. The system of claim 1, wherein the sleeve fits coaxially over the hub and over the injection end shield.

7. A passive safety shield system for an injection pen needle, comprising:
   a needle hub
   a needle mounted on the hub and having an injection end and a non-injection end, wherein the hub has a recess surrounding the non-injection end of the needle to receive a pen-injector;
   an injection end shield moving coaxially on the hub and having an aperture to permit passage of the needle through the injection end shield;
   a substantially tubular sleeve moving coaxially on the hub;
   a shield fastening element on the sleeve cooperating with a corresponding element on the injection end shield to fasten the injection end shield to the sleeve;
   a hub fastening element on the sleeve cooperating with a corresponding element on the hub to fasten the hub to the sleeve;
   a spring biasing the injection end shield toward the injection end of the pen needle;

wherein the sleeve is engaged with the hub and the injection end shield to hold the injection end shield in a position covering the injection end of the needle before an injection, and to lock the injection end shield in a position covering the injection end after an injection or in the event of an accidental use;

further comprising a non-injection end shield situated on the hub and having an aperture to permit passage of the non-injection end of the needle;

at least one engaging element on the non-injection end shield engaging a corresponding element on the hub;

wherein, when the pen-injector is removed from the hub, the engaging element on the non-injection end shield cooperates with the corresponding element on the hub to lock the non-injection end shield in a position covering the non-injection end of the needle, and wherein threads on the pen injector mate with the threads on the non-injection end shield.

* * * * *